(12) United States Patent
Küspert (10) Patent No.: US 10,478,135 B2
(45) Date of Patent: Nov. 19, 2019

(54) UROLOGY TABLE WITH TILTABLE X-RAY TUBE

(71) Applicant: Storz Medical AG, Tägerwilen (CH)

(72) Inventor: Alexander Küspert, Kesswil (CH)

(73) Assignee: STORZ MEDICAL AG, Tagerwilen (CH)

( * ) Notice: Subject to any disclaimer, the term of this patent is extended or adjusted under 35 U.S.C. 154(b) by 263 days.

(21) Appl. No.: 15/609,390

(22) Filed: May 31, 2017

(65) Prior Publication Data

US 2017/0347978 A1     Dec. 7, 2017

(30) Foreign Application Priority Data

Jun. 6, 2016   (EP) ..................................... 16173033

(51) Int. Cl.
*A61B 6/04*     (2006.01)
*A61B 6/00*     (2006.01)

(52) U.S. Cl.
CPC .......... *A61B 6/0407* (2013.01); *A61B 6/4208* (2013.01); *A61B 6/4452* (2013.01); *A61B 6/5205* (2013.01); *A61B 6/54* (2013.01)

(58) Field of Classification Search
CPC ........... A61B 6/00; A61B 6/04; A61B 6/0407; A61B 6/54; A61B 6/4208; A61B 6/4452; A61B 6/5205; A61B 6/02; A61B 6/025; A61B 6/03; A61B 6/032; A61B 6/035

USPC ....... 378/4, 11, 17, 21, 25, 26, 62, 146, 197, 378/205, 209

See application file for complete search history.

(56) References Cited

U.S. PATENT DOCUMENTS

| | | | |
|---|---|---|---|
| 2005/0058257 A1 | 3/2005 | Fischer et al. | |
| 2011/0062343 A1 | 3/2011 | Kato | |
| 2015/0289828 A1* | 10/2015 | Foland | A61B 6/4233 378/62 |

FOREIGN PATENT DOCUMENTS

| | | |
|---|---|---|
| DE | 9012435 U1 | 1/1992 |
| DE | 19843680 C1 | 2/2000 |
| EP | 2609859 A1 | 7/2013 |

\* cited by examiner

*Primary Examiner* — Jurie Yun
(74) *Attorney, Agent, or Firm* — Quarles & Brady LLP; Yakov S. Sidorin (57) ABSTRACT

A urological device include a patient table with longitudinal and broad sides, and an X-ray imaging system containing an X-ray source and an X-ray detector for detecting the X-ray radiation emitted by the X-ray source towards the patient on the patient table. A first linear drive is provided for moving the X-ray source parallel to the broad side and a second linear drive is provided for moving the X-ray detector parallel to the broad side, but in an opposite direction. A dedicated pivoting mechanism is configured to pivot the X-ray source around a first pivot axis.

13 Claims, 6 Drawing Sheets

UROLOGY TABLE WITH TILTABLE X-RAY TUBE

CROSS-REFERENCE TO RELATED APPLICATIONS

This application claims priority from pending European Application No. 16173033.8, filed on Jun. 6, 2016. The disclosure of the priority application is incorporated by reference herein in its entirety.

BACKGROUND

1. Field of the Invention

The invention relates to a device including a urology table for Percutaneous Nephrolithotomy (PCNL) surgery of the human or animal body. Such a device includes a radiologic system, which allows to survey the surgery. Percutaneous Nephrolithotomy (PCNL) is the preferred technique for treating large stones (over 2 cm in diameter) in the kidney. It involves keyhole surgery performed through a small incision in the skin overlying the kidney. During the surgery, X-ray images are made in order to locate the position of the operating instruments in relation to the kidney stones.

2. Description of Relevant Art

A commonality shared by the surgical systems in the field of urology is that the X-ray source and the X-ray detector have to be pivoted around the patient in a common orbit. This is necessary to make X-ray images of a subject in different orientations, for example to allow to survey a surgery and to detect the exact position(s) of operating instruments.

The state of the art describes two different types of X-ray systems. The first type includes C-arm systems. Here, the X-ray source is located at one end of a C-arm, and the X-ray detector is at the other side opposed to the X-ray source. Both may be rotated around a virtual center axis. The movement of the whole X-ray system is necessary in order to prevent image distortions and to allow pictures from different angles and positions. The surgeon and the operating room personal are limited in their freedom of movement by the C-arm of the X-ray system.

The second type includes systems with a focus on ergonomic concentrated, fatigue-free work. These systems have an X-ray detector located in a position within or under the patient table. The X-ray source is located on a support, which is normally configured as an arm above the patient table and opposite to the X-ray detector. An electromechanical system in the surgery system allows pivoting and tilting the patient table into multiple positions in order to provide optimal working conditions for the doctor and his/her assistants, as well as a comfortable access position for the patient by changing the height of the table. The X-ray source and the X-ray detector are configured to be tilted synchronously, so that they are facing each other in every state or position.

U.S. Pat. No. 7,942,575 B2 discloses a urological X-ray workstation with an X-ray source and an X-ray detector. The X-ray workstation as well as the X-ray source are supported on device retainers of a device carrier, which is located at the longitudinal side of a patient positioning table such that the X-ray source and the X-ray detector can be positioned opposite one another and independently from one another in various orientations on an orbit that proceeds around a common center in a working plane (the working plane is oriented orthogonally to the longitudinal axis of the patient positioning table). The disadvantage of this contraption stems from a complex, large, and heavy X-ray tube mount and a complex and expensive X-ray receiver positioning system.

SUMMARY

The embodiments of the inventions are aimed at the goal of providing an improved urological X-ray system and/or urology table with X-ray system, which allows an improved treatment procedure without the spatial restrictions of a mobile C-arm system and which simultaneously allows for an ergonomic concentrated, fatigue-free work. The disclosed X-ray system and/or urology table with X-ray system should has a simple and light-weight mechanical design, which consumes less space and offers the surgeon an expanded freedom of movement. Furthermore, manufacturing costs associated with the production of an embodiment of the invention are decreased in comparison with those of related art.

A first embodiment relates to a urological radiology device. The device includes a patient table, an X-ray source and an X-ray detector. It may additionally include at least one X-ray source support configured to hold the device.

For easier reference in the following description, a Cartesian coordinate system is defined. The point of origin of such Cartesian coordinate system preferably is arranged in the center of the upper surface of the patient table. X-axis and y-axis are in a plane defined by the patient table. The x-axis is parallel to a longitudinal side of the patient table. The y-axis is parallel to a broad side of the patient table. The longitudinal side is longer than the broad side. The z-axis points upwards and is orthogonal to the x-y plane.

The X-ray source, which preferably is an X-ray tube and which may include a high voltage power supply, is held above the patient table by an X-ray source support. The X-ray source support is preferably configured to allow movement of the X-ray source in a first plane parallel to and above the x-y plane with the use of at least one X-ray source linear drive. Most preferably, such linear drive is additionally configured to provide for a translational movement parallel to the y-axis, in y direction.

The X-ray source may be aligned to emit an X-ray beam of X-ray radiation in the direction of a patient table and, when the patient is on the table, through the patient. For improved alignment, the X-ray source may be appropriately equipped with a pivoting means (such as a rotatable shaft) to be pivotable around a first pivot axis. This configuration allows for keeping the X-ray beam aligned with respect to the patient (patient table) and/or the X-ray detector, even when the X-ray tube is being translated. Therefore, it is possible to orient the X-ray source to direct the X-ray beam from different angles and positions to the patient (patient table) at any time. The X-ray source preferably has an X-ray beam collimator.

The X-ray radiation, once emitted, can be detected with an X-ray detector unit, which preferably includes a planar detector within or under the patient table. The X-ray detector may be appropriately equipped with a repositioner to be moveable in a second plane that is parallel to the patient table. At least one X-ray detector linear drive is provided to move the X-ray detector and to align the X-ray detector with respect to the X-ray source to receive the emitted X-ray beam.

Alternatively, the X-ray source and the X-ray detector may be moved such that a desired region or section of the patient positioned on the table is projected onto the detector. Most preferably, the same region of the patient on the patient table may be projected from different angles to the X-ray detector. Therefore, the X-ray source must be aligned with the X-ray detector in each position. This structural configuration allows taking X-ray images of the patient at different angles. Furthermore, it allows using a much simpler and cheaper mechanical mounting and bearing of the detector and the X-ray source.

To coordinate the movement of at least two linear movement mechanisms of the X-ray source and the X-ray detector and the pivot mechanism of the X-ray source, a control unit may be additionally provided. The control unit may be in practice connected to the X-ray source linear drive, the pivot mechanism, and the detector linear drive—preferably by at least one control cable. The control unit may be configured to coordinate the X-ray source linear drive, the pivot mechanism, and the detector linear drive as explained above. Alternatively, it may assert control signals, such that at least 50 percent of radiation contained in the X-ray beam be collected by the X-ray detector. In a situation when not all of the X-ray beam hits the detector, the beam's dimension has to be appropriately reduced by the collimator in such a way as to be fully received by the detector.

Preferably, the alignment of the X-ray source and the X-rays detector is carried out such that the center of the X-ray beam is aligned to the center of the X-ray detector and with a certain region of the patient to be imaged. It may be desirable to have a plurality of X-ray images of the same region from different directions.

There may be further included a means for adaptation or change of an X-ray dose, to compensate for variation of the distance between the X-ray source and the X-ray detector with position. Therefore, in one implementation, the X-ray dose may be adapted or varied depending on the mutual positioning of the X-ray source and the detector to ensure a constant level of X-ray energy at the detector. Furthermore, the adaptation may be appropriately coordinated to be made dependent on the patient characteristics.

As the X-ray detector is not tilted, there may be a keystone distortion present in images generated by the X-ray detector in a lateral state of the X-ray source, when the X-ray source is not directly above the X-ray detector but is laterally shifted in a plane parallel to the plane of the table. If present, such keystone distortion may be corrected digitally, with an image-processing unit (such as a programmable processor or computer).

A basic unit may provide housing for a power supply, the image processing computer, a master control system, and mechanical systems configured to adjust position of at least one attachment part (such as, for example, the X-ray source support).

A patient table may be attached to the basic unit via an X-ray source support. In one implementation, the patient table is designed to receive a patient thereon preferably in a treatment position. The patient table may be made of carbon composite, glass fiber composite material, or any other kind of X-ray transmissive material. In a related embodiment, the patient table may be positioned on an independent stand or foot. The device carrier and the patient table may be configured to be height-adjustable and pivotable around an axis of rotation to allow for an ergonomic positioning of the patient and for the surgeon, and to allow for easy handling of the patient during the surgery.

The X-ray detector preferably is a flat panel detector. The detector may work based on GDO2 (Gadolinium dioxide) or CsJ (Cesiumjodide). The X-ray image data generated by the X-ray detector is further transferred to an image-processing computer. The X-ray detector may be configured to be part of the patient table or may be part of a separate unit that is disposed below the patient table and that may be attached to the X-ray source support or to an extra stand or foot of the patient table. The patient table may be structured to be moveable, independently from the X-ray detector, in parallel to the x and/or y-axes.

In one case, the X-ray source is supported by the X-ray source support, which may be a stand-alone, independent support standing at or attached to the ground. In a preferred embodiment, the X-ray source support comprises a first support section, a second support section, and a third support section. Preferably, the second support section is attached orthogonally to a first support section in z-direction. Alternatively, the second support section may be attached to the patient table in z-direction. The third support section may be attached at one end to the second support section parallel to the first support section (y-direction). The third support section may be structured to be height adjustable in the direction of the z-axis. Preferably, this section may be moveable by a linear moving means, in parallel to the y-axis. The other end of the third support section, holding the X-ray tube may be located above the patient table preferably opposite to the X-ray detector. Most preferably, the second and/or third support sections are moveable in a plane parallel to that of the patient table.

Another embodiment of the invention relates to a method for recording a plurality of X-ray images of the target (such as same area of the patient's body) at or from different angles. The method includes at least one of the following steps:

Positioning an X-ray source in a first position above a patient table to face an X-ray detector that is disposed within or under the patient table (such that, in operation, the X-ray source emits the X-rays towards or in the direction of the X-ray detector).

Generating an X-ray beam with the X-ray source and generating a first X-ray image of a section of a target (for example, a patient) on the patient table with the X-ray detector.

Moving/displacing the X-ray source parallel to a y-axis (that is preferably in a plane of the patient table and parallel to a broad side of the patient table) with an X-ray source linear drive to a second position and pivoting the X-ray source with a pivoting means to align the X-ray beam with the contours or bounds of the target (the patient body).

Moving the X-ray detector parallel to the y-axis in a direction opposite to the direction of displacement of the X-ray source to align the X-ray detector with the X-ray beam.

Generating another X-ray beam with the X-ray source and generating a second X-ray image of a section of a patient on the patient table (and, in a specific case, the second image of the same section) with the X-ray detector.

Furthermore, a multi-view image or a 3-D image may be generated from the first X-ray image and the second X-ray image and/or further X-ray images as a result of image data processing with a programmable processor.

BRIEF DESCRIPTION OF THE DRAWINGS

In the following, the invention will be described by way of example, without limitation of the general inventive concept, on examples of embodiment and with reference to the drawings.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION

Figure 1:
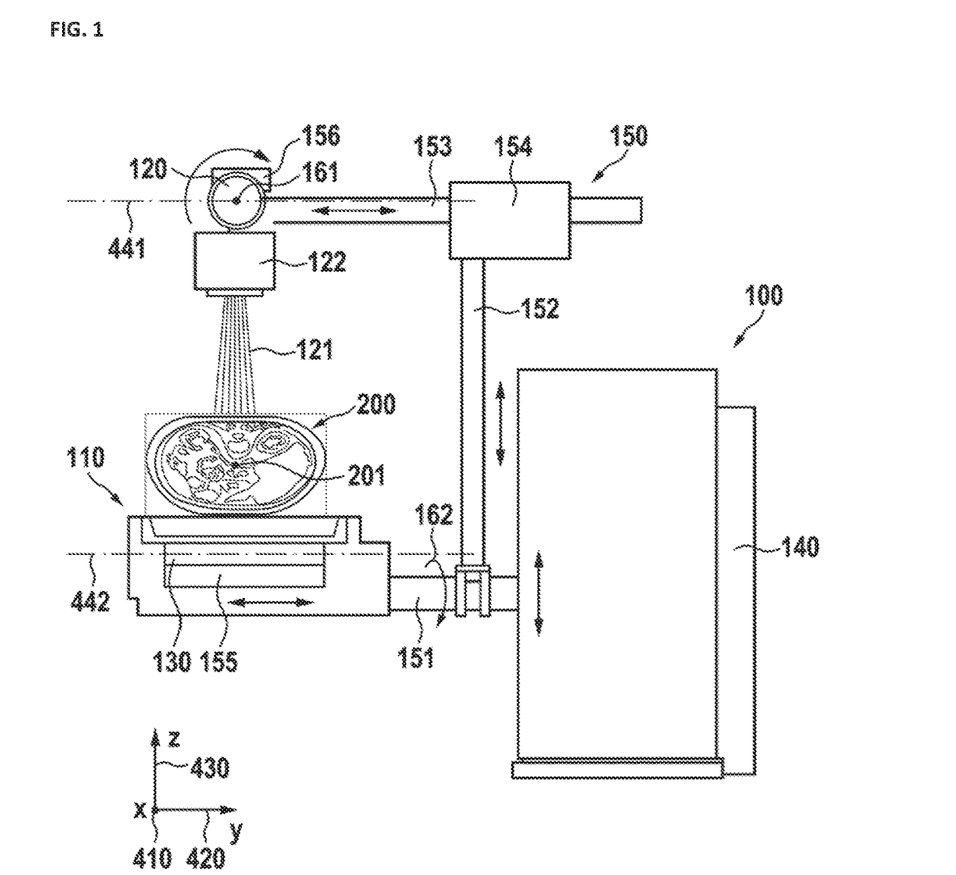
FIG. 1 shows a first embodiment of a urological device.

FIG. 1 shows a first embodiment of a urological device. The device includes a patient table 110, an X-ray source 120, and an X-ray detector 130. In a preferred embodiment, it may further include at least one X-ray source support 150 for holding the whole device, as well as a basic unit 140 configured to provide housing for a power supply, the image processing computer, a master control system and mechanical systems for adjusting the position of at least one attachment part for example the X-ray source support 150.

For easier reference of the following, a Cartesian coordinate system is defined. The point of origin of the Cartesian coordinate system preferably is arranged in the center of the upper surface of the patient table. (For a better clarity of the drawings, the axes of the coordinate system in the drawings is shown below the patient table.) X-axis 410 and y-axis 420 are in a plane defined by the patient table. The x-axis 410 is parallel to a longitudinal side of the patient 110 table and the y-axis 420 is parallel to a broad side of the patient table. The z-axis 430 points upwards and is orthogonal to the x-y plane.

The X-ray source 120 is held above the patient table 110 by an X-ray source support 150 and is translatable in a plane 441 parallel to the x-y plane and along the z-axis by an X-ray source linear drive 154.

Additionally the X-ray source 120 may be structured to be pivotable about a pivot axis 161 such as to align the X-ray source to emit an X-ray beam 121 in the direction of patient 200 on the patient table 110. The X-ray source preferably has a collimator 122 for beam forming.

An X-ray detector 130 within, or under, the patient table 110 is disposed to detect the X-ray radiation. The X-ray detector may be moveable in a second plane parallel to the x-y plane and the patient table 110. At least one X-ray detector linear drive 155 allows for the X-ray detector 130 to be aligned with respect to the X-ray beam 121 and, preferably, with respect to the center of the X-ray beam. Thus, X-ray images from different angles of the same region of the patient 200 can be recorded (for example, to survey the surgery procedure).

The patient table 110 may be attached to the basic unit 140 via an X-ray source support 150 (as shown—to a part 151 of the X-ray source support), which, in turn, may be attached to the basic unit 140. The patient table 110 may be moveable independent from the X-ray detector 130 parallel to the x 410 and y-axis 420. The X-ray source support 150 comprises a first support section 151, a second support section 152, and a third support section 153. The second support section 152 is attached orthogonally to a first support section 151, along the z-axis. The third support section 153 may be attached with one end to the second support section 152, parallel to the first support section 151 (which extends in y-direction, 420). The third support section 153 may be configured to be height adjustable (in the direction of the z-axis 430). Preferably, it may be moveable by the X-ray source linear drive 154 parallel to the y-axis 420. Another end of the third support section 153, holding the X-ray 120 tube, may be located above the patient table 200 preferably opposite to and above the X-ray detector 130. Most preferably, the second 152 and/or third support 153 sections are configured to be moveable in a plane parallel to the plane of the patient table 200.

The X-ray detector preferably is a flat panel detector 130. The detector may be based on $GDO_2$ (Gadolinium dioxide) or CsJ (Cesiumjodide). The X-ray image data generated by the X-ray detector 130 may be transferred to an image-processing computer (not shown).

Figure 2:
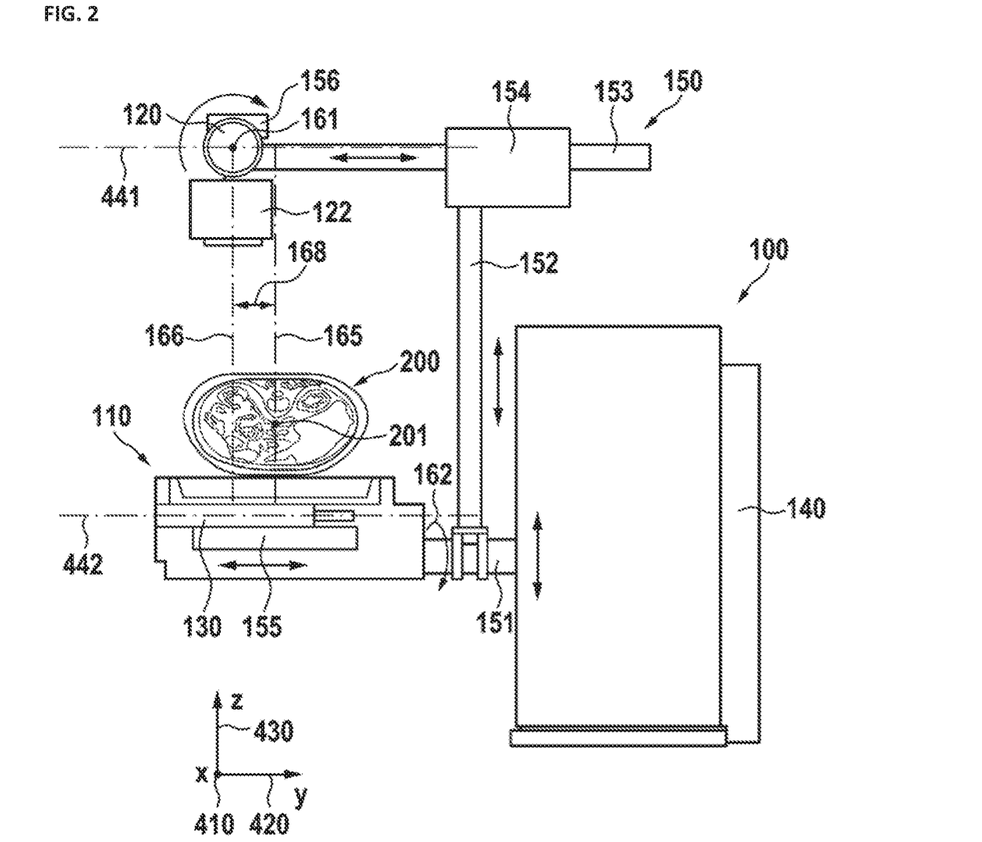
FIG. 2 shows a related embodiment.

FIG. 2 shows a related embodiment. Here, the X-ray source 120 and the X-ray detector 130 are shown moved in the same direction and by the same distance from the first centerline 165. As a result, a desired region or section of the patient 200 that is different from the center of the patient 201, is projected to the X-ray detector 130. Therefore, as shown, the center line 166 representing the center/axis of the X-ray beam 122, does not run through the center 201 of the patient 200. Instead, there is a lateral offset 168 between the first centerline 165, which runs through the center 201 of the patient 200 and the third centerline 166. As shown, the X-ray source 120 and the X-ray detector 130 may be in a position facing each other. This movability/repositioning of the X-ray source 120 and the X-ray detector 130 allows to irradiate and image various parts of the patient 200 without the necessity of moving the patient 200 or changing the position of the patient table 110.

Figure 3:
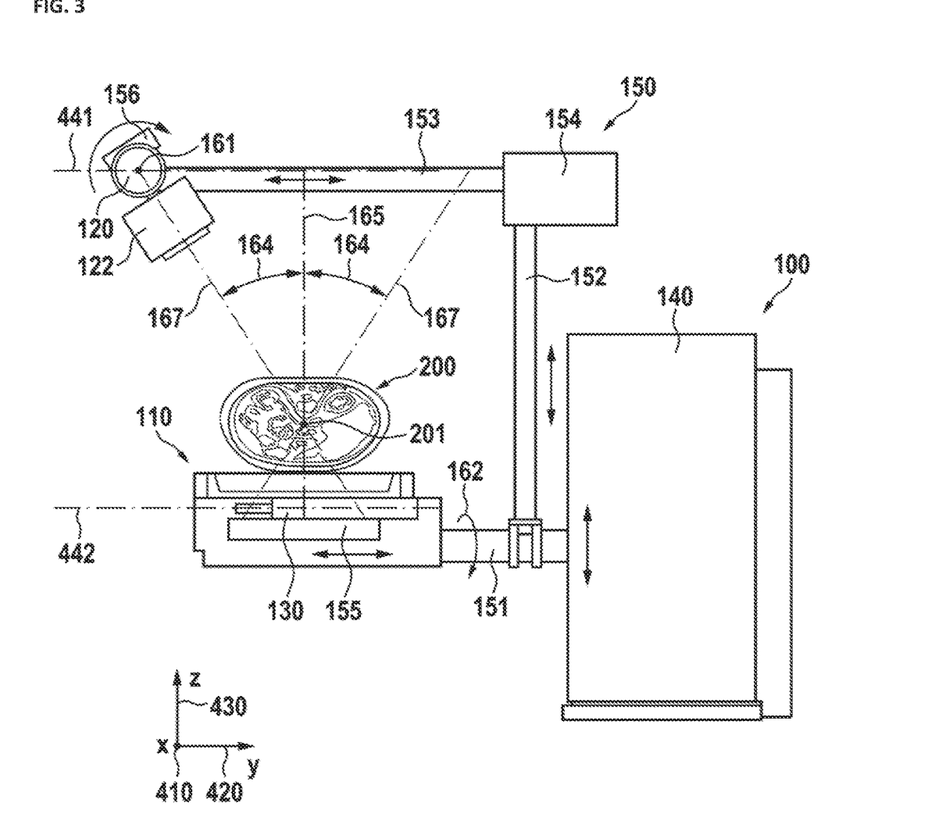
FIG. 3 shows the device with displaced and tilted X-ray tube.

FIG. 3 shows the same urology device 100 as that of FIG. 1, but with a laterally displaced and tilted X-ray tube. The X-ray source 120 is displaced parallel to the y-axis 420 with respect to the center 201 of the target (patient) 200 and therefore is laterally offset from the center 201 of the patient 200. The X-ray source 120 is tilted around the first pivot axis 161.

The X-ray detector 130 has been moved in a direction opposite to the direction of displacement of the X-ray source 120, and parallel to the y-axis 420. By doing so, X-ray images of the center 201 of the patient 200 or of other target portions of the patient 200 may be procured from different perspectives or angles 164. Therefore, multiple images can be composed into a 3-D image.

To obtain a good alignment of the X-ray source 120 and the X-ray detector 130, preferably the X-ray source 120 is moved in the first plane 441 parallel to the patient table 110, while the X-ray detector 130 is moved in the second plane 442 parallel to the patient table 110 in an opposite direction. The distances of movement of the X-ray tube 120 and the X-ray detector 130 may be adjusted as required to preferably align the X-ray beam, emitted by the X-ray source, at the center of the X-ray detector 130.

The center of the X-ray beam 121 in a center position of the X-ray source 120 and the X-ray detector 130 is defined by a first centerline 165. In a lateral position of the X-ray source, the center of the X-ray beam 121 is defined by a second centerline 167. The angle 164 between the first centerline 165 and the second centerline 167 may be up to 40 degrees, and preferably 30 degrees. The patient table 110 may be moveable independently from the X-ray detector 130 in directions of the x-axis 410 and y-axis 420. The patient 110 table may also be pivotable or rotatable about a second pivot axis 162.

In addition, a number of different images may be made from different angles 164 as shown above in FIG. 3 by moving the X-ray source 120 and the X-ray detector 130 in opposite directions.

Figure 4:
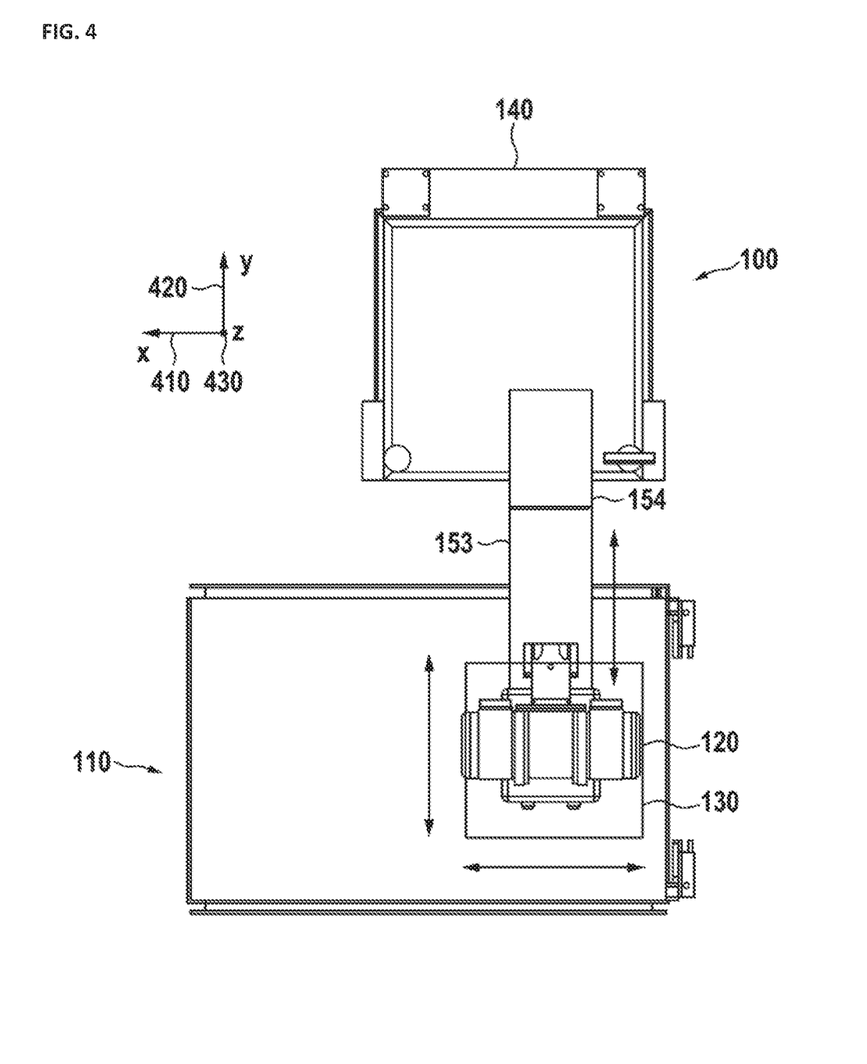
FIG. 4 shows the device from a top view.

FIG. 4 presents a top view of the urology device 100 from FIG. 1. The urology device 100 comprises a patient table 110, a basic unit 140, an X-ray source 120 and an X-ray detector 130.

Figure 5:
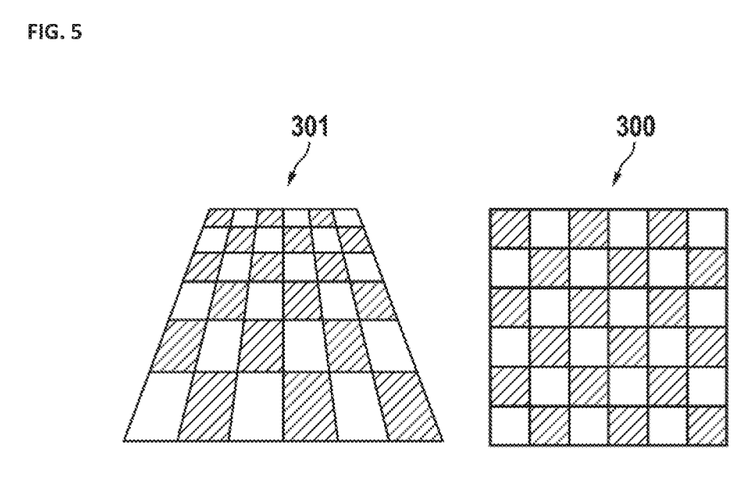
FIG. 5 shows a keystone distorted picture and a corrected one.

FIG. 5 presents two illustrations 300, 301. The first illustration 300 depicts an image of a scene in a state where the X-ray source 120 and the X-ray detector 130 are facing each other. In this state, there is no keystone distortion. In the other operational state of the device (which corresponds to, for example, FIG. 3) there is a keystone distortion of the X-ray image of the scene, as shown. The keystone distortion has to be corrected by digital post processing.

Figure 6:
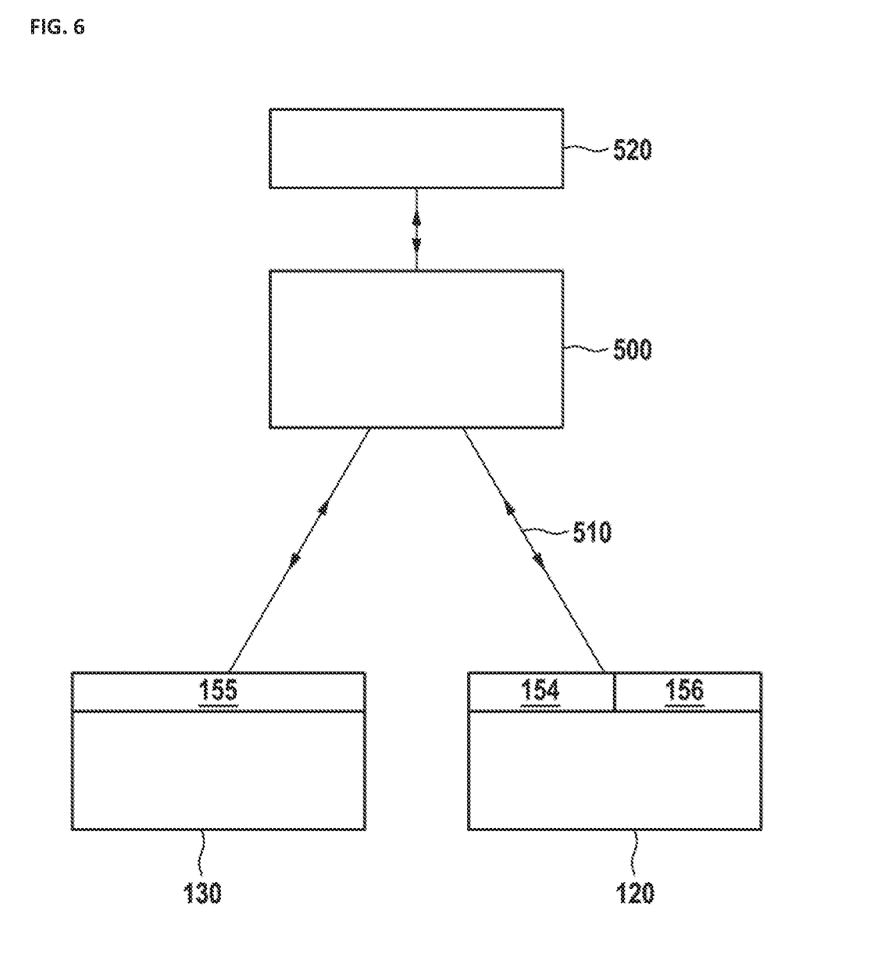
FIG. 6 shows a block diagram of the movement control.

FIG. 6 illustrates a control unit 500 for the at least two linear movement mechanisms 154, 155 of the X-ray source 154 and the X-ray detector 155, and the pivot mechanism 156 of the X-ray source 120. The control unit may be connected to the X-ray source linear drive 154, the pivot mechanism 156, and the detector linear drive 154 preferably by at least one control cable 510. The control unit 500 may be configured to coordinate the operation(s) of the X-ray source linear drive 154, the pivot mechanism 156, and the detector linear drive 155 as explained above. Preferably, the X-ray beam is aligned to, or preferably centered on the X-ray detector. Alternatively, it may provide control signals, such that the X-ray detector may collect at least 50 percent of the X-ray beam. Nevertheless, if not the complete X-ray beam hits the detector is has be reduced in size by the collimator in such a way, that now x-ray can pass next the detector. Additionally an external control 520 can be connected to the control unit 500. The external control can be a manual control and/or a master computer. The control unit 500 may be part of the basic unit 140 or the master computer. The communication between the different parts can be a unidirectional communication or bidirectional communication.

It will be appreciated to those skilled in the art having the benefit of this disclosure that this invention is believed to provide a device including a urology table for Percutaneous Nephrolithotomy (PCNL) surgery. Modifications and alternative embodiments of various aspects of the invention can be made without deviation from the scope of the invention. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

LIST OF REFERENCE NUMERALS

100 Urology device
110 Patient table
120 X-ray source
121 X-ray beam
122 Collimator
130 X-ray detector
140 Basic unit
150 X-ray source support
151 First support section
152 Second support section
153 Third support section
154 X-ray source linear drive
155 X-ray detector linear drive
156 Pivot mechanism
161 First pivot axis
162 Second pivot axis
164 Interior angle
165 First centerline
166 Third centerline
167 Second centerline
168 Offset
200 Patient
201 Center
300 Image
301 Image with keystone distortion
410 x-axis, direction
420 Y-axis, direction
430 z-axis, direction
441 First plane (X-ray tube)
442 Second plane (X-ray detector)
500 Control unit
510 Control cable
520 External control

The invention claimed is:

1. A urological device oriented with respect to a Cartesian system of coordinates defined by an x-axis, a y-axis, and a z-axis, the device comprising:
   a patient table having a longitudinal side aligned with the x-axis, and a broad side aligned with the y-axis, wherein the z-axis extends above and below the patient table in a direction transverse to the patient table;
   an X-ray source mounted above the patient table and configured to emit a beam of X-ray radiation directed to the patient table,
   an X-ray detector mounted below the patient table and configured to detect the X-ray radiation that has been emitted by the X-ray source and that has passed through a patient on the patient table,
   an X-ray source linear drive configured to move the X-ray source parallel to the y-axis,
   a pivot mechanism configured to pivot the X-ray source about a first pivot axis and in a plane parallel to the y-axis and z-axis,
   an X-ray detector linear drive configured to move the X-ray detector parallel to the y-axis without tilting the X-ray detector,
   and
   a control unit operably connected with the X-ray detector and X-ray source and configured to coordinate
   (i) a first movement of the X-ray source in a first direction with
   a unidirectional second movement of the X-ray detector in a second direction that is opposite to the first direction, and
   (ii) pivoting of the X-ray source to position the X-ray source for directing the X-ray beam to the detector at different angles,
   such as to have a center of the X-ray beam aligned with a center of the X-ray detector at each position of the X-ray detector.

2. The urological device according to claim 1, configured to coordinate the movements of the X-ray detector and the X-ray source to deliver the X-ray, emitted by the X-ray source, to the center of the X-ray detector at different angles to procure a three-dimensional image of a chosen location of a patient, when the patient is disposed on the patient table, from multiple images of said chosen location that have been obtained at said different angles, respectively.

3. The urological device according to claim 1, configured to coordinate the movements of the X-ray detector and of the X-ray source to have the center of the X-ray beam aligned with a pre-determined fixed location at the patient table for each position of the X-ray detector to form an image of the same location of a patient disposed on the patient table at each position of the X-ray detector.

4. The urological device according to claim 1, wherein the X-ray detector is a flat panel detector.

5. The urological device according to claim 1, wherein the X-ray detector is mounted to the patient table.

6. The urological device according to claim 1, wherein the X-ray detector is configured to be moved in one or more of the following regimes: (i) in a plane parallel to the patient table and (ii) parallel to any of the x-axis and the y-axis.

7. The urological device according to claim 1, wherein the X-ray source is configured to be moved in any of the following regimes: (i) in a plane parallel to the patient table and (ii) parallel to any of the x-axis and the y-axis.

8. The urological device according to claim 1, wherein the patient table is structured to be moved parallel to the x-axis and the y-axis and independently from a movement of the X-ray detector.

9. The urological device according to claim 1, wherein the patient table comprises at least one of carbon composite material, glass fiber composite material, and another X-ray transmissive material.

10. A method for operating a urological device, comprising:
positioning an X-ray source in a first position above a patient table to direct an X-ray beam, emitted by the X-ray source in operation, to an X-ray detector disposed within or under the patient table,
wherein the patient table has a longitudinal side aligned with an x-axis and a broad side aligned with a y-axis, a z-axis being transverse to a surface of the patient table, wherein said x-axis, y-axis, and z-axis aggregately define a chosen Cartesian coordinate system,
generating the X-ray beam with the X-ray source, and generating a first X-ray image of a first region of a patient when the patient is positioned on the patient table with the X-ray detector,
moving the X-ray source parallel to the y-axis with an X-ray source linear drive to a second position, and pivoting the X-ray source by a pivoting mechanism to align a center of the X-ray beam with the first region of the patient at every position of the X-ray source while
unidirectionally moving the X-ray detector parallel to the y-axis in a direction opposite to a direction of moving the X-ray source without tilting the X-ray detector, to have a center of the X-ray detector aligned with the center of the X-ray beam at every position of the X-ray detector.

11. The method for operating a urological device according to claim 10, further comprising:
after said moving the X-ray detector and said moving the X-ray source, and after said generating the X-ray beam, generating a second X-ray image of a second region of the patient when the patient is positioned on the patient table with the X-ray detector.

12. The method according to claim 11, wherein said generating the second X-ray image includes generating the second X-ray image of the second region, wherein the second region is the same as the first region.

13. The method according to claim 10, further comprising:
creating a 3-D image from multiple X-ray images of the first region acquired at different angles of incidence of the X-ray at the first region.

* * * * *